(12) United States Patent
Ben-Tsur et al.

(10) Patent No.: US 11,510,590 B1
(45) Date of Patent: Nov. 29, 2022

(54) METHODS AND SYSTEMS FOR TREATING GASTROINTESTINAL DISORDERS

(71) Applicant: VIBRANT LTD., Yokneam (IL)

(72) Inventors: Lior Ben-Tsur, Netanya (IL); Shalom Lampert, Maalot (IL)

(73) Assignee: Vibrant Ltd., Yokneam (IL)

( * ) Notice: Subject to any disclaimer, the term of this patent is extended or adjusted under 35 U.S.C. 154(b) by 874 days.

(21) Appl. No.: 16/403,553

(22) Filed: May 5, 2019

Related U.S. Application Data

(60) Provisional application No. 62/667,648, filed on May 7, 2018.

(51) Int. Cl.
*A61B 5/07* (2006.01)
*A61B 5/00* (2006.01)

(52) U.S. Cl.
CPC ............ *A61B 5/073* (2013.01); *A61B 5/6861* (2013.01); *A61B 2562/162* (2013.01)

(58) Field of Classification Search
CPC ...................................................... A61B 5/073
See application file for complete search history.

(56) References Cited

U.S. PATENT DOCUMENTS

| | | |
|---|---|---|
| 3,485,235 A | 12/1969 | Felson |
| 4,239,040 A | 12/1980 | Hosoya et al. |
| 4,507,115 A | 3/1985 | Kambara et al. |
| 5,170,801 A | 12/1992 | Casper et al. |
| 5,991,931 A | 11/1999 | Hawkins et al. |
| 6,453,199 B1 | 9/2002 | Kobozev |
| 6,632,216 B2 | 10/2003 | Houzego et al. |
| 6,687,537 B2 | 2/2004 | Bernabei |
| 6,776,165 B2 | 8/2004 | Jin |
| 6,911,004 B2 | 6/2005 | Kim et al. |
| 6,929,363 B2 | 8/2005 | Sakai et al. |
| 6,984,205 B2 | 1/2006 | Gazdzinski |
| 7,076,284 B2 | 7/2006 | Segawa et al. |
| 7,354,397 B2 | 4/2008 | Fujita et al. |

(Continued)

FOREIGN PATENT DOCUMENTS

| | | |
|---|---|---|
| CN | 1829466 A | 9/2006 |
| CN | 101810481 A | 8/2010 |

(Continued)

OTHER PUBLICATIONS

Processing of Polymer Matrix Composites Containing CNTs Dec. 1, 2015 by Marcio Loos (Federal University of Santa Catarina).

(Continued)

*Primary Examiner* — Travis R Hunnings
(74) *Attorney, Agent, or Firm* — Momentum IP; Marc Van Dyke

(57) ABSTRACT

A method for treating a human subject suffering from a gastrointestinal disorder using a non-dissolvable ingestible capsule, the method including providing the non-dissolvable ingestible capsule to the subject, and subsequently, ingesting the non-dissolvable ingestible capsule by the subject, wherein passage of the non-dissolvable ingestible capsule through the gastrointestinal tract of the subject treats the gastrointestinal disorder, and wherein the non-dissolvable ingestible capsule may be at least one of: a non-vibrating capsule, a capsule that is devoid of any electronic components, and a capsule that is devoid of any mechanical moving components.

6 Claims, 2 Drawing Sheets

(56) References Cited

U.S. PATENT DOCUMENTS

| | | | |
|---|---|---|---|
| 7,510,537 B2 | 3/2009 | Imboden et al. |
| 7,511,733 B2 | 3/2009 | Takizawa et al. |
| 7,623,904 B2 | 11/2009 | Uchiyama et al. |
| 7,637,864 B2 | 12/2009 | Yokoi et al. |
| 7,686,788 B2 | 3/2010 | Freyman et al. |
| 7,797,033 B2 | 9/2010 | DAndrea et al. |
| 7,942,811 B2 | 5/2011 | Segawa et al. |
| 8,021,356 B2 | 9/2011 | Uchiyama et al. |
| 8,021,357 B2 | 9/2011 | Tanaka et al. |
| 8,021,384 B2 | 9/2011 | Weiss et al. |
| 8,036,748 B2 | 10/2011 | Zdeblick et al. |
| 8,038,600 B2 | 10/2011 | Uchiyama et al. |
| 8,147,482 B2 | 4/2012 | Shimizu et al. |
| 8,202,697 B2 | 6/2012 | Holmes |
| 8,216,130 B2 | 7/2012 | Glukhovsky et al. |
| 8,295,932 B2 | 10/2012 | Bitton et al. |
| 8,306,592 B2 | 11/2012 | Takizawa et al. |
| 8,518,022 B2 | 8/2013 | Trovato et al. |
| 8,597,278 B2 | 12/2013 | Trovato et al. |
| 8,701,677 B2 | 4/2014 | Duan et al. |
| 8,755,888 B2 | 6/2014 | Voznesensky et al. |
| 8,771,730 B2 | 7/2014 | Navon et al. |
| 8,852,172 B2 | 10/2014 | Dijksman et al. |
| 8,945,005 B2 | 2/2015 | Hafezi et al. |
| 9,078,799 B2 | 7/2015 | Shohat et al. |
| 9,156,169 B2 | 10/2015 | Duan et al. |
| 9,232,909 B2 | 1/2016 | Duan et al. |
| 9,511,211 B2 | 12/2016 | Tange et al. |
| 9,532,923 B2 | 1/2017 | Shohat et al. |
| 9,538,937 B2 | 1/2017 | Rohde et al. |
| 9,572,746 B2 | 2/2017 | Asfora |
| 9,707,150 B2 | 7/2017 | Shabbat |
| 9,730,336 B2 | 8/2017 | Arneson et al. |
| 9,750,923 B2 | 9/2017 | Niichel et al. |
| 9,770,588 B2 | 9/2017 | Bettinger |
| 9,919,152 B2 | 3/2018 | Levine et al. |
| 9,986,898 B2 | 6/2018 | Duan et al. |
| 9,999,415 B2 | 6/2018 | Duan et al. |
| 10,070,854 B2 | 9/2018 | Duan et al. |
| 10,076,234 B2 | 9/2018 | Duan et al. |
| 10,118,035 B2 | 11/2018 | Perez et al. |
| 10,143,364 B2 | 12/2018 | Duan et al. |
| 10,172,598 B2 | 1/2019 | Amoako-Tuffour et al. |
| 10,314,514 B2 | 6/2019 | Duan |
| 10,369,463 B2 | 8/2019 | Barney et al. |
| 10,478,047 B2 | 11/2019 | Duan et al. |
| 10,478,373 B2 | 11/2019 | Duan et al. |
| 10,500,127 B2 | 12/2019 | Duan et al. |
| 10,517,466 B2 | 12/2019 | Ye et al. |
| 10,531,788 B2 | 1/2020 | Wang et al. |
| 10,537,720 B2 | 1/2020 | Ben-Tsur |
| 10,543,348 B2 | 1/2020 | Ben-Tsur |
| 10,869,811 B2 | 12/2020 | Duan et al. |
| 10,874,339 B2 | 12/2020 | Chavan et al. |
| 10,888,277 B1 | 1/2021 | Ben-Tsur et al. |
| 10,905,378 B1 | 2/2021 | Ben-Tsur et al. |
| 2002/0055734 A1 | 5/2002 | Houzego et al. |
| 2002/0099310 A1 | 7/2002 | Kimchy et al. |
| 2002/0103417 A1 | 8/2002 | Gazdzinski |
| 2002/0132226 A1 | 9/2002 | Nair et al. |
| 2002/0147466 A1 | 10/2002 | Bernabei |
| 2003/0020810 A1 | 1/2003 | Takizawa et al. |
| 2003/0073935 A1 | 4/2003 | Segawa et al. |
| 2003/0191430 A1 | 10/2003 | DAndrea et al. |
| 2004/0030454 A1 | 2/2004 | Kim et al. |
| 2004/0050394 A1 | 3/2004 | Jin |
| 2004/0253304 A1 | 12/2004 | Gross et al. |
| 2004/0267240 A1 | 12/2004 | Gross et al. |
| 2005/0058701 A1 | 3/2005 | Gross et al. |
| 2005/0085696 A1 | 4/2005 | Uchiyama et al. |
| 2005/0148847 A1 | 7/2005 | Uchiyama et al. |
| 2005/0177069 A1 | 8/2005 | Takizawa et al. |
| 2006/0062852 A1 | 3/2006 | Holmes |
| 2006/0094992 A1 | 5/2006 | Imboden et al. |
| 2006/0169293 A1 | 8/2006 | Yokoi et al. |
| 2006/0200083 A1 | 9/2006 | Freyman et al. |
| 2006/0211963 A1 | 9/2006 | Spirk et al. |
| 2006/0270899 A1 | 11/2006 | Amirana |
| 2006/0276729 A1* | 12/2006 | Reed .................. A61H 23/0263 601/46 |
| 2007/0015952 A1 | 1/2007 | Chang et al. |
| 2007/0032699 A1 | 2/2007 | Segawa et al. |
| 2007/0123809 A1 | 5/2007 | Weiss et al. |
| 2007/0178160 A1* | 8/2007 | Burnett .................. A61B 5/4238 424/484 |
| 2007/0213659 A1 | 9/2007 | Trovato et al. |
| 2007/0238940 A1* | 10/2007 | Amirana ............. A61B 5/4839 600/302 |
| 2007/0299301 A1 | 12/2007 | Uchiyama et al. |
| 2008/0051635 A1 | 2/2008 | Tanaka et al. |
| 2008/0065168 A1 | 3/2008 | Bitton et al. |
| 2008/0161639 A1 | 7/2008 | Katayama et al. |
| 2008/0188837 A1 | 8/2008 | Belsky et al. |
| 2008/0269664 A1 | 10/2008 | Trovato et al. |
| 2008/0275430 A1 | 11/2008 | Belsky et al. |
| 2008/0281238 A1 | 11/2008 | Oohashi et al. |
| 2009/0043278 A1 | 2/2009 | Tanaka et al. |
| 2009/0275923 A1 | 11/2009 | Shimizu et al. |
| 2009/0281380 A1 | 11/2009 | Miller et al. |
| 2009/0306632 A1 | 12/2009 | Trovato et al. |
| 2009/0306633 A1 | 12/2009 | Trovato et al. |
| 2009/0318783 A1 | 12/2009 | Rohde et al. |
| 2009/0318841 A1* | 12/2009 | Shohat .................. A61H 21/00 601/46 |
| 2010/0039616 A1 | 2/2010 | Yumikake et al. |
| 2010/0049012 A1 | 2/2010 | Dijksman et al. |
| 2010/0217079 A1 | 8/2010 | Tichy |
| 2010/0222670 A1 | 9/2010 | Demierre et al. |
| 2010/0312228 A1 | 12/2010 | Zdeblick et al. |
| 2010/0324381 A1 | 12/2010 | Glukhovsky et al. |
| 2011/0117192 A1 | 5/2011 | Navon et al. |
| 2011/0208011 A1 | 8/2011 | Ben-Horin |
| 2011/0240044 A1 | 10/2011 | Duan et al. |
| 2011/0319727 A1 | 12/2011 | Ishihara |
| 2013/0158452 A1 | 6/2013 | Juto et al. |
| 2013/0213495 A1 | 8/2013 | Huang et al. |
| 2013/0253387 A1 | 9/2013 | Bonutti et al. |
| 2013/0267788 A1 | 10/2013 | Duan et al. |
| 2014/0107726 A1 | 4/2014 | Voznesensky et al. |
| 2014/0187907 A1 | 7/2014 | Duan et al. |
| 2014/0221741 A1 | 8/2014 | Wang et al. |
| 2014/0247039 A1 | 9/2014 | Duan et al. |
| 2014/0288470 A1 | 9/2014 | Asfora |
| 2015/0011829 A1 | 1/2015 | Wang et al. |
| 2015/0011874 A1 | 1/2015 | Amoako-Tuffour et al. |
| 2015/0018614 A1 | 1/2015 | Duan et al. |
| 2015/0018615 A1 | 1/2015 | Duan et al. |
| 2015/0045658 A1 | 2/2015 | Tange et al. |
| 2015/0065926 A1 | 3/2015 | Nakamura et al. |
| 2015/0073315 A1* | 3/2015 | Shabbat ............. A61H 23/02 601/46 |
| 2015/0088222 A1 | 3/2015 | Bettinger |
| 2015/0223727 A1 | 8/2015 | Kimchy et al. |
| 2015/0313792 A1 | 11/2015 | Shohat et al. |
| 2015/0380140 A1 | 12/2015 | Duan et al. |
| 2016/0121111 A1 | 5/2016 | Levine et al. |
| 2016/0136104 A1 | 5/2016 | Niichel et al. |
| 2016/0183878 A1 | 6/2016 | Weast et al. |
| 2016/0287058 A1 | 10/2016 | Ye et al. |
| 2016/0303133 A1 | 10/2016 | Dudley et al. |
| 2016/0310357 A1 | 10/2016 | Duan et al. |
| 2017/0020374 A1 | 1/2017 | Duan et al. |
| 2017/0021172 A1 | 1/2017 | Perez et al. |
| 2017/0035407 A1 | 2/2017 | Duan et al. |
| 2017/0035520 A1 | 2/2017 | Duan et al. |
| 2017/0135897 A1 | 5/2017 | Shohat et al. |
| 2017/0151423 A1 | 6/2017 | Vandierendonck et al. |
| 2017/0231865 A1* | 8/2017 | Stronks .................. A61F 9/08 601/46 |
| 2017/0273863 A1 | 9/2017 | Shabbat |
| 2017/0296425 A1 | 10/2017 | Duan et al. |
| 2017/0296428 A1 | 10/2017 | Duan et al. |
| 2017/0340242 A1 | 11/2017 | Duan |
| 2018/0055597 A1 | 3/2018 | Duan et al. |

(56) References Cited

U.S. PATENT DOCUMENTS

| | | |
|---|---|---|
| 2018/0084975 A1 | 3/2018 | Duan et al. |
| 2018/0168490 A1 | 6/2018 | Jones et al. |
| 2018/0185238 A1 | 7/2018 | Ilan |
| 2018/0360355 A1 | 12/2018 | Chavan et al. |
| 2019/0224070 A1 | 7/2019 | Ben-Tsur et al. |
| 2019/0307999 A1 | 10/2019 | Ben-Tsur |
| 2019/0308002 A1 | 10/2019 | Ben-Tsur |
| 2020/0315541 A1 | 10/2020 | Ben-Tsur et al. |

FOREIGN PATENT DOCUMENTS

| | | |
|---|---|---|
| CN | 102743174 A | 10/2012 |
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105380777 A | 3/2016 |
| CN | 105411505 A | 3/2016 |
| CN | 205108749 U | 3/2016 |
| CN | 205286889 U | 6/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |
| CN | 107375951 A | 11/2017 |
| EP | 2987447 A1 | 2/2016 |
| EP | 2995240 A1 | 3/2016 |
| JP | 2001062397 A | 3/2001 |
| JP | 2002163359 A | 6/2002 |
| JP | 2005052502 A | 3/2005 |
| JP | 2010503451 A | 2/2010 |
| JP | 2010246703 A | 11/2010 |
| JP | 2013535756 A | 9/2013 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2013121276 A1 | 8/2013 |
| WO | 2018055487 A1 | 3/2018 |

OTHER PUBLICATIONS

Comparison of pharmacokinetic profile of levodopa throughout the day between levodopa/carbidopa/entacapone and Tevodopa/carbidopa when administered four or five times daily Mar. 1, 2009 European Journal of Clinical Pharmacology 65(5):443-55 Kuoppamäki et al.
CN101810481 Machine Translation (by Google Translate)—published Aug. 25, 2010.
CN102743174 Machine Translation (by Google Translate)—published Jun. 29, 2016.
CN102743175 Machine Translation (by Google Translate)—published Oct. 24, 2012.
CN102743176A Machine Translation (by Google Translate)—published Oct. 24, 2012.
CN102813515 Machine Translation (by Google Translate)—published Dec. 12, 2012.
CN102860810 Machine Translation (by Google Translate)—published Oct. 29, 2014.
CN104898850 Machine Translation (by Google Translate)—published Feb. 6, 2018.
CN103222842 Machine Translation (by Google Translate)—Sep. 9, 2015.
CN105025245 Machine Translation (by Google Translate)—published Nov. 4, 2015.
CN105079970 Machine Translation (by Google Translate)—published Jun. 19, 2018.
CN105380777 Machine Translation (by Google Translate)—published Oct. 27, 2017.
CN105411505 Machine Translation (by Google Translate)—published Aug. 23, 2019.
CN105939451 Machine Translation (by Google Translate)—published Oct. 2, 2018.
CN105942959 Machine Translation (by Google Translate)—published Aug. 24, 2018.
CN105996961 Machine Translation (by Google Translate)—published May 11, 2018.
CN106056588 Machine Translation (by Google Translate)—published Oct. 26, 2016.
CN106137760 Machine Translation (by Google Translate)—published Nov. 23, 2016.
CN106097335B Machine Translation (by Google Translate)—published Jan. 25, 2019.
CN106204599B Machine Translation (by Google Translate)—published Apr. 26, 2019.
CN106373137 Machine Translation (by Google Translate)—published Jan. 4, 2019.
CN106923787 Machine Translation (by Google Translate)—published Jul. 7, 2017.
CN106934799 Machine Translation (by Google Translate)—published Sep. 3, 2019.
CN107174188 Machine Translation (by Google Translate)—published Sep. 19, 2017.
CN107233580 Machine Translation (by Google Translate)—published Mar. 2, 2021.
CN107240091 Machine Translation (by Google Translate)—published Sep. 3, 2019.
CN107375951B Machine Translation (by Google Translate)—published Apr. 2, 2021.
CN1829466B Machine Translation (by Google Translate)—published Jan. 5, 2011.
CN202483565 Machine Translation (by Google Translate)—published Oct. 10, 2012.
CN202699138 Machine Translation (by Google Translate)—published Jan. 30, 2013.
CN202821355 Machine Translation (by Google Translate)—published Mar. 27, 2013.
CN202843564 Machine Translation (by Google Translate)—published Apr. 3, 2013.
CN202843608 Machine Translation (by Google Translate)—published Apr. 3, 2013.
CN202875332 Machine Translation (by Google Translate)—published Apr. 17, 2013.
CN203634116 Machine Translation (by Google Translate)—published Jun. 11, 2014.
CN205108749 Machine Translation (by Google Translate)—published Mar. 30, 2016.
CN205286889 Machine Translation (by Google Translate)—published Jun. 8, 2016.
CN205758500 Machine Translation (by Google Translate)—published Dec. 7, 2016.

(56) References Cited

OTHER PUBLICATIONS

CN205913317 Machine Translation (by Google Translate)—published Feb. 1, 2017.
CN205928774 Machine Translation (by Google Translate)—published Feb. 8, 2017.
JP2001062397 Machine Translation (by Google Translate)—published Mar. 13, 2001.
JP2002163359A Machine Translation (by Google Translate)—published Jun. 7, 2002.
JP2005052502 Machine Translation (by Google Translate)—published Aug. 10, 2006.
JP2010246703 Machine Translation (by Google Translate)—published Nov. 4, 2010.
JP2010503451 Machine Translation (by Google Translate)—published Nov. 21, 2012.
JP2013535756 Machine Translation (by Google Translate)—published Sep. 25, 2014.

* cited by examiner

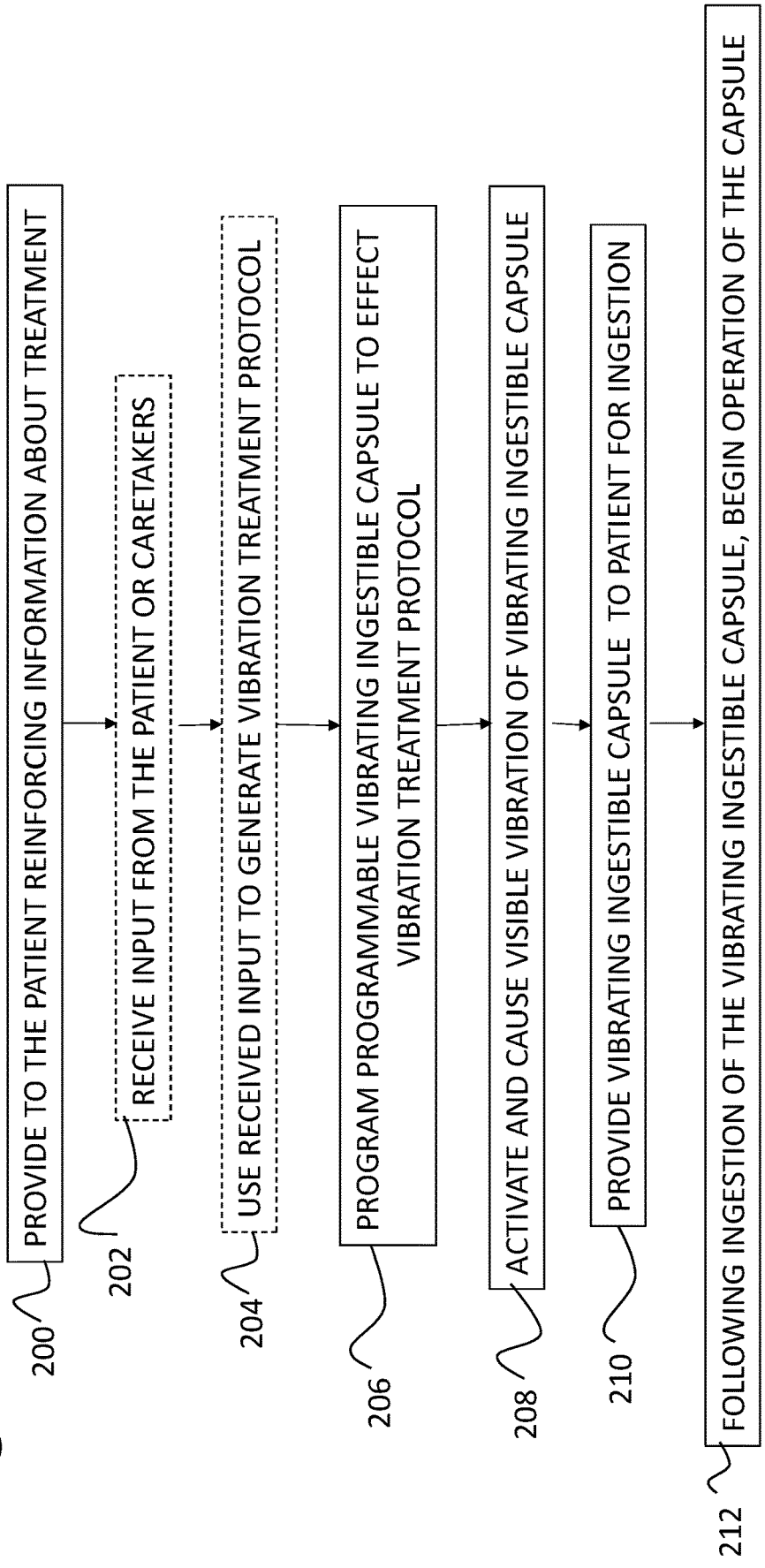

METHODS AND SYSTEMS FOR TREATING GASTROINTESTINAL DISORDERS

RELATED APPLICATIONS

The present application gains priority from US Provisional Patent Application No. 62/667,648 filed May 7, 2018 and entitled METHODS AND SYSTEMS FOR TREATING GASTROINTESTINAL DISORDERS, which is incorporated herein by reference as if fully set forth herein.

FIELD OF THE INVENTION

The present invention relates in general to medical devices, particularly to methods and systems for treating disorders of the gastrointestinal tract, such as chronic or acute constipation.

SUMMARY OF THE INVENTION

In accordance with embodiments of the present invention, there is provided a method for treating a subject, typically a human subject, suffering from a gastrointestinal disorder using a non-dissolvable ingestible capsule, the method including:

providing the non-dissolvable ingestible capsule to the subject; and subsequently, ingesting the non-dissolvable ingestible capsule by the subject, wherein passage of the non-dissolvable ingestible capsule through the gastrointestinal tract of the subject treats the gastrointestinal disorder.

In some embodiments, the non-dissolvable ingestible capsule is at least one of: a non-vibrating capsule; a capsule that is devoid of any electronic components; and a capsule that is devoid of any mechanical moving components.

In some embodiments, the non-dissolvable capsule includes a spherical capsule having a capsule diameter.

In some embodiments, the non-dissolvable capsule includes an elongated capsule arranged along a longitudinal axis and having a circular cross section in a direction perpendicular to the longitudinal axis, the circular cross section having a capsule diameter.

In some embodiments, a length of the non-dissolvable capsule, along the longitudinal axis, is in the range of 3 mm-30 mm, 3 mm-29 mm, 3 mm-28 mm, 3 mm-27 mm, 3 mm-26 mm, 3 mm-25 mm, 3 mm-24 mm, 3 mm-23 mm, 3 mm-22 mm, 3 mm-21 mm, 3 mm-20 mm, 4 mm-20 mm, 5 mm-20 mm, 6 mm-20 mm, or 7 mm-20 mm.

In some embodiments, the capsule diameter is not smaller than 3 mm, not smaller than 4 mm, not smaller than 5 mm, not smaller than 6 mm, or not smaller than 7 mm.

In some embodiments, the capsule diameter is not greater than 15 mm, not greater than 14 mm, not greater than 13 mm, not greater than 12 mm, or not greater than 11 mm.

In some embodiments, the capsule diameter is within the range of 3 mm-15 mm, 3 mm-14 mm, 3 mm-13 mm, 3 mm-12 mm, 3 mm-11 mm, 4 mm-15 mm, 4 mm-14 mm, 4 mm-13 mm, 4 mm-12 mm, 4 mm-11 mm, 5 mm-15 mm, 5 mm-14 mm, 5 mm-13 mm, 5 mm-12 mm, 5 mm-11 mm, 6 mm-15 mm, 6 mm-14 mm, 6 mm-13 mm, 6 mm-12 mm, 6 mm-11 mm, 7 mm-15 mm, 7 mm-14 mm, 7 mm-13 mm, 7 mm-12 mm, or 7 mm-11 mm.

In some embodiments, the non-dissolvable capsule is a non-vibrating capsule.

In some embodiments, the non-dissolvable capsule is devoid of any electronic components.

In some embodiments, the non-dissolvable capsule is devoid of any mechanical moving components.

In some embodiments, the non-dissolvable ingestible capsule includes a vibrating ingestible capsule operative in accordance with a vibration protocol, which vibration protocol is devoid of vibrations within the gastrointestinal tract of the subject.

In some embodiments, the method further includes, prior to the ingesting, triggering demonstrative vibrations of the vibrating ingestible capsule in the presence of the subject, such that the subject observes or feels the demonstrative vibrations.

In some embodiments, the method further includes pre-programming the vibrating ingestible capsule with the vibration protocol prior to the triggering.

In some embodiments, the method further includes providing to the vibrating ingestible capsule, using a control unit functionally associated with the vibrating ingestible capsule, information or an instruction regarding the vibration protocol.

In some embodiments, the information regarding the vibration protocol includes an indication or selection of a specific vibration protocol pre-programmed into the vibrating ingestible capsule.

In some embodiments, the control unit generates the vibration protocol and provides the vibration protocol to the vibrating ingestible capsule as the information.

In some embodiments, the control unit receives, prior to generating the vibration protocol, input relating to at least one desired parameter of treatment with the vibrating ingestible capsule, and generates the vibration protocol based on the received input.

In some embodiments, the at least one desired parameter includes at least one of a desired vibration intensity, a desired vibration frequency, a desired length of vibration, and a desired delay time prior to initiating vibration.

In some embodiments, the input is received from the subject.

In some embodiments, the input is received from at least one of a medical practitioner treating the subject, and a medical facility at which the subject is treated.

In some embodiments, the control unit provides the vibration protocol by remotely transmitting the vibration protocol to the vibrating ingestible capsule.

In some embodiments, the control unit provides the vibration protocol by transmitting to the vibrating ingestible capsule a list of vibration parameters for effecting the vibration protocol.

In some embodiments, the control unit provides the vibration protocol by transmitting to the vibrating ingestible capsule executable code for effecting the vibration protocol.

In some embodiments, the method further includes prior to the subject ingesting the non-dissolvable ingestible capsule, providing to the subject reinforcing information about treatment with the non-dissolvable ingestible capsule.

In some embodiments, the method further includes engaging the subject in at least one psychosomatic neutralizing activity relating to the non-dissolvable ingestible capsule.

In some embodiments, the gastrointestinal disorder includes at least one of acute constipation, chronic constipation, and gastroparesis.

In some embodiments, the providing and the ingesting together form a treatment session, and wherein the method includes administering to the subject at least one treatment session.

In some embodiments, the administering to the subject at least one treatment session includes administering to the subject a plurality of treatment sessions.

In some embodiments, the administering a plurality of treatment sessions includes administering at least one the treatment session per week, over a treatment period of at least two weeks, at least at least three weeks, at least four weeks, at least five weeks, at least six weeks, or at least eight weeks.

In some embodiments, the administering at least one treatment session per week includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

In some embodiments, a greater number of the plurality of treatment sessions achieve further improvement in symptoms of the gastrointestinal disorder.

In some embodiments, the method further includes, at a different time from the administering the at least one treatment session, administering to the subject at least one active treatment session using a vibrating ingestible capsule, the administering the at least one active treatment session including:
  providing the vibrating ingestible capsule to the subject, the capsule including:
    a housing;
    a battery, disposed within the housing; and
    a vibrating agitation mechanism, powered by the battery, the vibrating agitation mechanism adapted such that, in a first vibrating mode of operation, the housing exerts vibrations on an environment surrounding the capsule;
  ingesting the vibrating ingestible capsule by the subject; and
  following ingestion of the vibrating ingestible capsule by the subject, controlling the vibrating agitation mechanism such that the vibrating ingestible capsule vibrates in the first vibrating mode of operation when the capsule is disposed within a targeted zone within a gastrointestinal tract of the subject.

In some embodiments, the method includes administering the at least one treatment session at least once per week and administering the at least one active treatment session at least once per week.

In some embodiments, the method includes administering an equal number of treatment sessions and active treatment sessions per week.

In some embodiments, the method includes administering a different number of treatment sessions and active treatment sessions per week.

In some embodiments, the administering at least one treatment session and at least one active treatment session includes alternating, in time, administering of the at least one treatment session and of the at least one active treatment session.

In some embodiments, the administering at least one treatment session and the at least one active treatment session includes initially administering at least two treatment sessions in sequence, and subsequently administering at least one active treatment session.

In some embodiments, the administering at least one treatment session and at least one active treatment session includes initially administering at least two active treatment sessions in sequence, and subsequently administering at least one treatment session.

In some embodiments, the administering at least one treatment session and at least one active treatment session includes initially administering at least one treatment session and subsequently administering at least two active treatment sessions in sequence.

In some embodiments, the administering at least one treatment session and at least one active treatment session includes initially administering at least one active treatment session and subsequently administering at least two treatment sessions in sequence.

In accordance with additional embodiments of the present invention, there is provided a method for treating a human subject suffering from a gastrointestinal disorder, the method including:
  administering to the subject at least one sham treatment session using a non-dissolvable ingestible capsule, including;
    providing the non-dissolvable ingestible capsule to the subject; and
    subsequently, ingesting the non-dissolvable ingestible capsule by the subject; and
  administering to the subject at least one active treatment session using a vibrating ingestible capsule, including:
    providing the vibrating ingestible capsule to the subject, the capsule including:
      a housing;
      a battery, disposed within the housing; and
      a vibrating agitation mechanism, powered by the battery, the vibrating agitation mechanism adapted such that, in a first vibrating mode of operation, the housing exerts vibrations on an environment surrounding the capsule;
    ingesting the vibrating ingestible capsule by the subject; and following ingestion of the vibrating ingestible capsule by the subject, controlling the vibrating agitation mechanism such that the vibrating ingestible capsule vibrates in the first vibrating mode of operation when the capsule is disposed within a targeted zone within a gastrointestinal tract of the subject.

In some embodiments, the method includes administering the at least one sham treatment session at least once per week and administering the at least one active treatment session at least once per week.

In some embodiments, the method includes administering the sham treatment session and the active treatment session an equal number of times per week.

In some embodiments, the method includes administering the sham treatment session and the active treatment session a different number of times per week.

In some embodiments, the administering at least one sham treatment session and at least one active treatment session includes alternating, in time, administering of the at least one sham treatment session and of the at least one active treatment session.

In some embodiments, the administering at least one sham treatment session and at least one active treatment session includes initially administering at least two sham treatment sessions in sequence, and subsequently administering at least one active treatment session.

In some embodiments, the administering at least one sham treatment session and at least one active treatment session includes initially administering at least two active treatment sessions in sequence, and subsequently administering at least one sham treatment session.

In some embodiments, the administering at least one sham treatment session and at least one active treatment session includes initially administering at least one sham treatment session and subsequently administering at least two active treatment sessions in sequence.

In some embodiments, the administering at least one sham treatment session and at least one active treatment session includes initially administering at least one active treatment session and subsequently administering at least two sham treatment sessions in sequence.

BRIEF DESCRIPTION OF THE FIGURES

The foregoing discussion will be understood more readily from the following detailed description of the invention, when taken in conjunction with the accompanying FIGS. 1-2), in which:

FIG. 2 is a schematic flowchart of a method for treatment of a disorder in the gastrointestinal tract of a subject according to the present invention.

DESCRIPTION OF THE PREFERRED EMBODIMENTS

Figure 1:
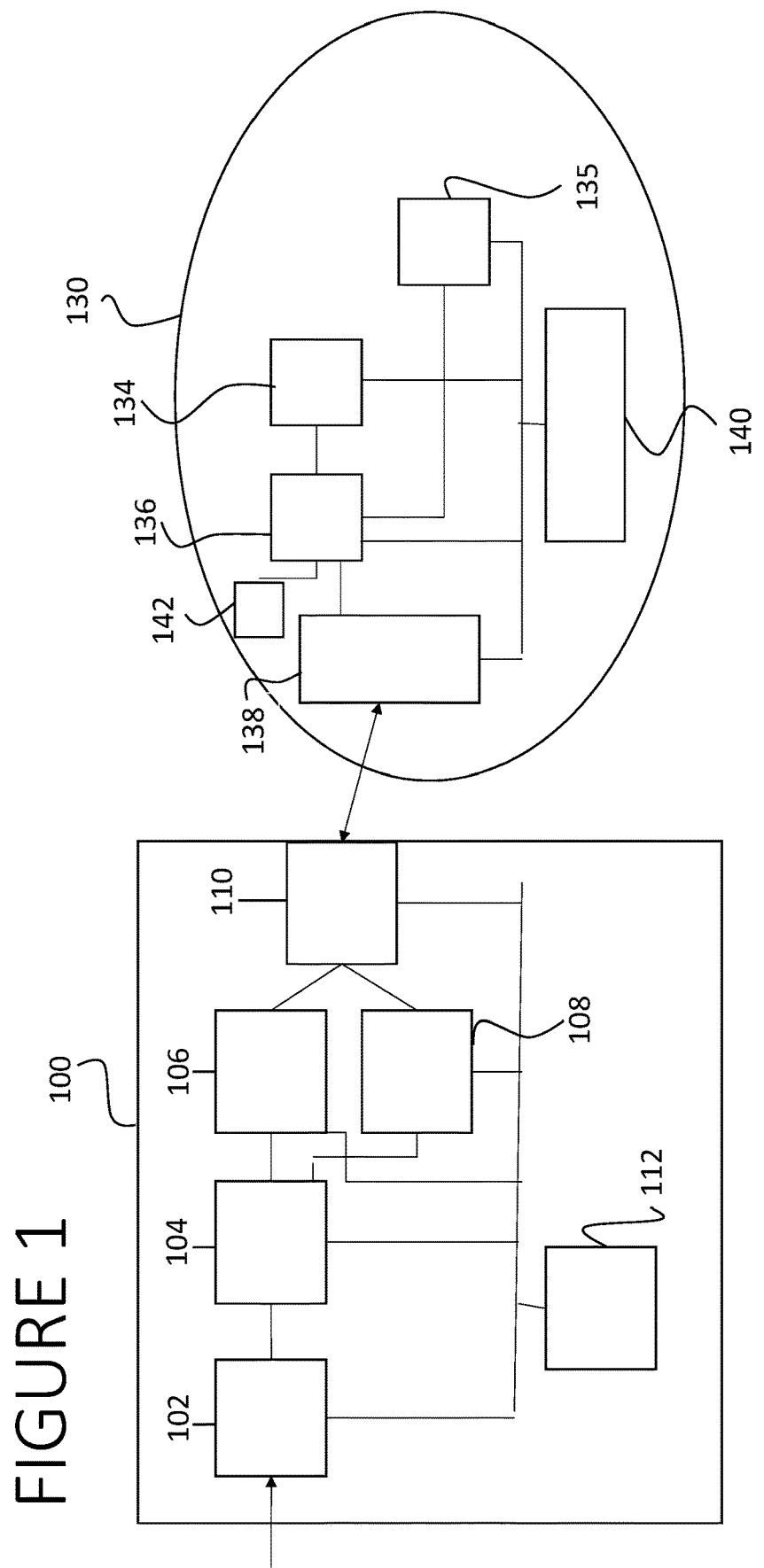
FIG. 1 is a schematic block diagram of a system for treatment of a disorder in the gastrointestinal tract of a subject according to an embodiment of the present invention.

The principles of the inventive system and methods for treatment of a disorder in the gastrointestinal tract of a subject, and specifically for treatment of ailments of the gastrointestinal tract, such as chronic constipation, acute constipation, or gastroparesis, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

It has long been known to medical personnel, and particularly to gastrointestinal specialists, that psychosomatics play a significant part in some disorders of the gastrointestinal tract, such as chronic constipation. In many cases, subjects suffering from chronic constipation have tried multiple treatment types, often having significant side effects, and which often afford little and/or diminishing relief.

It is further known that various medications and treatments currently available on the market have relatively low success rates, and relatively high incidence of side effects. For example, "Best Response Distribution of 12-Week Treatment with Prucalopride (RESOLOR) in patients with Chronic Constipation: Combined Results of Three Randomised, Double-Blind, Placebo-Controlled Phase III Trials" (*Gut* 2011 60: A159-A160) to Stanghellini et al, shows a success rate of approximately 23%, accompanied by a 15% side effect rate. In other words, 23% of the subjects participating in the study and treated with Prucalopride showed an increased rate to spontaneous bowel movements during the treatment period, but 15% of the subjects suffered from side effects, such as diarrhea.

Additionally, many currently available treatments, even when successfully treating the subject and providing an increase in the frequency of spontaneous bowel movements, tend to lose efficacy as the treatment continues, requiring increased dosages or transitioning to a new type of treatment, and often causing the subject pain or discomfort. Furthermore, such treatments typically treat the symptoms causing constipation and not the cause of constipation, and thus provide no relief to the subject once the treatment is stopped.

Another known characteristic of existing medications for treatment of constipation, is a placebo effect rate in the range of 3% to approximately 40%. For example, "Multicenter, 4-Week, Double-Blind, Randomized, Placebo-Controlled Trial of Lubiprostone, a Locally-Acting Type-2 Chloride Channel Activator, in Patients With Chronic Constipation" (*Am J Gastroenterol*. (2008) 103, 170-177) to Johanson et al describes a minimal placebo effect rate of 3.46%, and a maximal placebo effect rate of 36.9%. "Efficacy and safety of oral prucalopride in women with chronic constipation in whom laxatives have failed: an integrated analysis" (*UEG J* 2013: 1(1) 48-59) to Tack et al shows a minimal placebo effect rate of 11%, and a maximal placebo effect rate of 38.4%.

In light of all the limitations above, many subjects suffering from chronic constipation have a negative, or skeptical, attitude towards treatments offered to them by their medical practitioners.

The inventors have discovered that when subjects suffering from chronic constipation are treated with a vibrating capsule as described hereinbelow, the treatment success rate may be around 50% or even higher. Furthermore, the inventors have discovered that when the subjects saw the capsule vibrate prior to ingesting the capsule, and the capsule did not vibrate in their body, the placebo effect rate was higher than 35%.

The inventors have also discovered that a treatment including a non-dissolvable capsule and vibration result in a high response rate. The high success rates occur even without generation of a positive attitude of the subject, indicating that this is not a psychological effect (placebo effect) but rather a physiological effect that does not depend on the psychological state of the subject. The physiological aspect, as part of the treatment using a non-dissolvable capsule is further supported by the fact that the inventors have identified a dose response even when using the non-dissolvable capsule without vibration, for example as shown in Example 1 herein. In other words, when more non-dissolvable capsules are ingested per week, a greater percentage of the subjects see an improvement in their gastrointestinal disorder.

As such, a treatment method according to the present invention may include use of a non-dissolvable capsule alone, without vibration, or of a combination of non-vibrating non-dissolvable capsules together with vibrating capsules.

For the purposes of this application, the term "subject" relates to a human or mammal. Typically, the subject is a human.

For the purposes of this application, the term "patient" relates to a human or mammal suffering from an ailment of the gastrointestinal tract, such as chronic constipation. Typically, the patient is a human.

For the purposes of this application, the term "chronic constipation" relates to a spontaneous bowel movement (SBM) frequency of at most 3 SBMs per week, For the purposes of this application, the term "acute constipation" relates to a subject suffering from a specific event of constipation, without necessarily suffering from chronic constipation.

For the purposes of this application, the term "sham capsule" relates to any non-dissolvable ingestible capsule which may be ingested by a subject and which does not vibrate, or does not significantly vibrate, in the gastrointestinal tract of the user. In this context, a capsule is considered to "not significantly vibrate" in the gastrointestinal tract, and to be a sham capsule, even if the capsule vibrates for less than thirty minutes, more typically less than 20 minutes, in total, during its passage of the gastrointestinal tract, and/or if the capsule exerts less than 100 gr-force during vibration. Typically, the sham capsule is devoid of moving components and/or electronic components.

For the purposes of this application, the term "non-dissolvable capsule" relates to any capsule which does not dissolve under the conditions present in the gastrointestinal tract of a human. Typical materials of construction include polycarbonate and Polytetrafluoroethylene (PTFE).

For the purposes of this application, the term "sham capsule treatment" relates to treatment of a gastrointestinal disorder in a subject using one or more sham capsules, regardless of the subject observing any functionality of the capsule, information provided to the subject, the subject's psychological state, or the subject's assumptions regarding how the capsule is supposed to operate or what impact the capsule is supposed to have.

For the purposes of this application, the term "placebo effect" relates to a psychological effect, generated by the subject's attitude to a treatment or by the psychological state of the subject, such that the treatment shows clinical results.

For the purposes of this application, the term "placebo treatment" relates to treatment of a gastrointestinal disorder in a subject using a placebo capsule, a dissolvable ingestible capsule, while putting an emphasis on the psychological state of the subject and on the subject's beliefs with respect to the treatment, resulting in a psychosomatic improvement of the symptoms experienced by the subject.

For the purposes of this application, the term "active treatment" relates to treatment of a gastrointestinal disorder in a subject using a vibrating ingestible capsule, which is set to significantly vibrate in the subject's gastrointestinal tract following ingestion thereof. In this context, a capsule is considered to "significantly vibrate" in the gastrointestinal tract, and to provide an active treatment, if the capsule vibrates for at least 20 minutes, or at least 30 minutes, in total, during passage of the capsule through the gastrointestinal tract, and/or if the capsule exerts more than 100 gr-force during vibration.

For the purposes of this application, the term "placebo effect rate" relates to the percentage of subjects or patients in a study or medical trial, receiving a placebo treatment, who showed a positive response to the placebo as they were expected to show had they received the active treatment. Such a positive response may be expressed as an increase, of at least a threshold value, in the number of SBMs per unit time.

For the purposes of this application, the term "sham effect rate" relates to the percentage of subjects or patients in a study or medical trial, receiving a sham capsule (non-dissolvable capsule which does not vibrate in the gastrointestinal tract of the user), who showed a positive response to the treatment. Such a positive response may be expressed as an increase, of at least a threshold value, in the number of SBMs/CSBM per unit time.

For the purposes of this application, the term "attitude neutralizing activity" relates to an activity that at least removes the negative attitude, concern, stress, or worry associated with a treatment for chronic constipation, with possible side effects or placebo effect of such treatment, and possibly generates a positive attitude or expectation toward such treatment.

For the purposes of this application, the term "ingestible capsule" relates to a biocompatible capsule suitably sized for ingestion by a human subject or a human patient. The ingestible capsule may be a dissolvable ingestible capsule or a non-dissolvable ingestible capsule. An ingestible capsule may be formed of a housing and contents (which may be, for example, electronic components, organic materials, or air), or be devoid of contents, e.g., a biocompatible material that is uniformly or homogenously formed, through and through, and has a capsule-like shape.

For the purposes of this application, the term "vibrating ingestible capsule" relates to a non-dissolvable ingestible capsule adapted to vibrate, for a cumulative duration of at least one minute, in accordance with internal vibration parameters of the capsule. The vibration parameters of the capsule may be preprogrammed, or may be provided to the capsule by a suitable communication method or protocol. It will be noted that, depending on the treatment protocol of the vibrating ingestible capsule, the vibrating ingestible capsule may be used in an active treatment or in a sham capsule treatment.

For the purposes of this application, the term "short range wireless communication method" relates to any wireless communication method or protocol in which signals are communicated up to a maximum range of at most 1 kilometer or less, at most 500 meters, at most 300 meters, at most 200 meters, at most 100 meters, at most 50 meters, or at most 10 meters such as, for example, Bluetooth communication, Wi-Fi communication, RFID signal communication, and the like.

For the purposes of this application, the term "intermittent vibration motor" refers to a vibration motor which vibrates and is operative at certain times, and does not vibrate at other times, the activation times being selected by a processor or other control unit controlling the vibration motor.

For the purposes of this application, the terms "vibrating capsule", "vibrating ingestible capsule", and the like relate to capsule which includes a vibration motor and is capable of producing vibrations.

For the purposes of this application, two treatment sessions A and B are considered to be administered "in sequence" if no other treatment sessions are administered following administering of treatment session A and prior to administering treatment session B.

For the purposes of this application, treatment sessions A and B are "alternated" if treatment session A is administered, followed by administration of treatment session B without administration of other treatment sessions between treatment sessions A and B, and subsequently treatment session A is administered again without administration of other treatment sessions between treatment sessions B and A.

Referring now to the drawings, FIG. 1 is a schematic block diagram of a system for treatment of a disorder in the gastrointestinal tract of a subject according to an embodiment of the present invention.

As seen in FIG. 1, a control unit 100 includes a user input module 102, a processor 104, a programming module 106, and a verification and activation module 108. In some embodiments, the control unit 100 further includes a transceiver 110. The control unit further includes at least one power source 112 providing power to user input module 102, processor 104, programming module 106, verification and activation module 108, and/or transceiver 110.

It will be appreciated that control unit 100 may be any suitable control unit, including a suitably programmed computing device such as a smartphone, tablet computer, laptop computer, desktop computer, and the like, or may be a dedicated control unit, e.g. forming part of another medical device.

In some embodiments, control unit 100 is configured to control, program, verify, and/or activate a programmable vibrating ingestible capsule 130. Programmable vibrating ingestible capsule 130 includes a timer 134; a motor, such as an intermittent vibration motor 135; a controller 136, functionally associated with timer 134 and with vibration motor 135; a receiver or transceiver 138 functionally associated with the controller 136; and at least one power source 140 providing power to timer 134, vibration motor 135, controller 136, and/or receiver/transceiver 138.

Power source 140 may be any suitable power source, such as, for example, one or more alkaline or silver oxide batteries, primary batteries, rechargeable batteries, capacitors and/or super capacitors. Additional details and functionality of programmable vibrating ingestible capsule 130 are described hereinbelow.

The user input module 102 is configured to receive input from a user, be it input relating to the treatment, such as a desired vibration frequency, or input to facilitate tracking the effects of the treatment, such as information regarding the occurrence of a spontaneous bowel movement (in order to facilitate tracking of the frequency of spontaneous bowel movements).

The user input module 102 may be any suitable input module, and may include, for example, a keyboard, a pointing device such as a mouse, a touchscreen, or a touchpad configured to receive input entered directly by the subject, a caretaker of the subject, medical personnel treating the subject, or any other input provider.

In some embodiments, the control unit 100 further includes a display, functionally associated with the processor 104 and/or with the user input device, which display is adapted to exhibit to the user one or more questions to be answered, the answers provided as input to the user input module 102. For example, the display may exhibit a scale from 1-10, and ask the subject to indicate the desired vibration intensity by indicating a specific level on the scale, which indication may be provided to user input module 102.

As another example, the user input module may be operable by a medical practitioner or a caregiver of the subject.

Processor 104 is configured to receive the user input from user input module 102, and to use the received input to track the bowel movement frequency of the user, and/or to determine one or more characteristics of a desired treatment to be provided by a specific capsule, such as the vibration frequency, the vibration intensity, and the like. Based on the provided input and on pre-programmed information available to the processor 104, the processor may generate a vibration treatment protocol for the subject, the protocol including vibration parameters to be programmed into programmable vibrating ingestible capsule 130.

It will be appreciated that the generated vibration protocol may also be a placebo protocol, which, when programmed into capsule 130 does not cause the capsule 130 to vibrate following ingestion of the capsule, or would include minimal vibration following ingestion. In some embodiments of the placebo protocol, the capsule 130 may vibrate prior to ingestion thereof so that the subject sees, or feels, the capsule vibrate.

The programming module 106 is configured to receive the vibration treatment protocol from the processor 104, and to program controller 136 of programmable vibrating ingestible capsule 130 to implement the vibration treatment protocol upon activation thereof. In some embodiments, the programming module 106 includes, or is functionally associated with, a transmitter, such as transmitter/transceiver 110, for transmission of the vibration treatment protocol to the receiver/transceiver 138 of capsule 130.

In some embodiments, the programming module 106 transmits the protocol to the capsule 130 as a sequence of parameter signals, such as digits, indicating time frames from activation and vibration parameters to be used at those time frames. In some embodiments, the programming module 106 transmits the protocol to the capsule 130 as executable code to be used by the controller 136 to automatically activate vibration motor 135 in accordance with the protocol.

In some embodiments, controller 136 of capsule 130 is pre-programmed with a pre-defined vibration treatment protocol. In some such embodiments, the processor 104 need not generate a vibration treatment protocol, and programming module 106 need not program capsule 130, and may, in some embodiments, even be obviated.

In some embodiments, controller 136 of capsule 130 is pre-programmed with multiple pre-defined vibration treatment protocols. In some such embodiments, the processor 104 or programming module 106 may instruct the controller 136 of capsule 130 which of the vibration treatment protocols should be used.

In some embodiments, controller 136 of capsule 130 is pre-programmed with one or more pre-defined vibration treatment protocols each including one or more variables. In some such embodiments, processor 104 generates suitable values to be used for the variables, and programming module 106 programs the controller 136 with the selected values.

The activation module 108 is configured to activate the programmable vibrating ingestible capsule 130 for operation. In some embodiments, activation of the capsule 130 includes immediate activation of the timer 134 to start counting time (i.e., a countdown) until activation of the vibration motor. Such embodiments assume that the capsule 130 is activated shortly before the subject ingests the capsule.

In some embodiments, the activation module 108 includes, or is functionally associated with, a transmitter or transceiver such as transmitter/transceiver 110, and activates the capsule 130 by providing an activation signal thereto.

In some embodiments, the activation module 108 also includes a verification module, configured to verify that the capsule 130 received the vibration treatment protocol and is capable of effecting the protocol without error. In some embodiments, the verification module includes, or is functionally associated with a receiver, receiving from the capsule 130 a verification signal indicating that the capsule has received the protocol.

In some embodiments, the verifications signal comprises the capsule 130 vibrating in accordance with a specific vibration pattern indicative of verification thereof, the verification module includes a vibration sensor, sensing the vibration of the capsule 130.

In some embodiments, the vibration of the capsule 130 in accordance with a specific vibration pattern, is visible to the subject or otherwise observable thereby prior to ingestion of the capsule. In some embodiments, the display of the control unit 100 instructs the user to hold the capsule prior to providing the activation signal to the capsule 130, such that when the capsule 130 vibrates, the user feels the vibration in his hand.

In some embodiments, the input module 102 of control unit 100 is configured to continue receiving input from the subject regarding excretions or a frequency of excretions during and after treatment with the capsule 130. In such embodiments, processor 104 is further configured to use such additional input to identify a change in a frequency of excretions for the subject being treated, and/or to update the vibration treatment protocol for the subject based on such a change.

Reference is now made to FIG. 2, which is a schematic flowchart of a method for treatment of a disorder in the gastrointestinal tract of a subject according to the present invention. It will be appreciated that, for clarity, the method of FIG. 2 is described with respect to the system of FIG. 1, though it may be implemented using any suitable system, and implementation is not limited to the specific system shown in FIG. 1.

As seen at step 200, the subject may receive reinforcing information about the treatment, for example from medical personnel such as a nurse or a doctor, or independently by reading about the treatment or by watching a video clip or other media presentation about the treatment. Such reinforcing information may include: an indication of the clinically established success rate of treatment, shown by the inventors to be approximately 50% as compared to a success rate in the range of 20%-25% obtained by the currently available pharmaceutical treatments;

an indication of the lack of side effects during treatment with a vibrating ingestible capsule as described hereinabove; and/or an explanation of the method by which the vibrating ingestible capsule provides treatment, e.g., that the capsule is thought to generate naturally-occurring contractions within the gastrointestinal tract, and thus "reminds" the body how to function naturally, or otherwise induces the body to generate such spontaneous bowel movements.

As seen at step 202, the subject may provide input to processor 104 of control unit 100 regarding desired vibration parameters during treatment, for example via user input module 102. In some embodiments, parameters that may be provided by the user include vibration intensity, vibration frequency, length of vibration and/or delay time until vibration begins, within a predetermined range that would not disrupt the functionality of the capsule. For example, the display of control unit 100 may exhibit to the user a question, such as "what should the vibration intensity be for your capsule", and the user may be able to provide the input by selecting a desired vibration intensity, either between several discrete options, such as "low", "medium" and "high", or along a continuum, such as by setting a pointer to any point between the numbers 1 and 10, where 1 represents low intensity and 10 represents high intensity.

It will be appreciated that another person, such as a caretaker or medical practitioner, may provide the input to control unit 100 via the input module 102, provided that the input being provided is selected or controlled by the subject. For example, the subject's caretaker or medical practitioner may ask the subject what vibration intensity they desire, and then input the vibration intensity desired by the subject.

In some embodiments, processor 104 of control unit 100 may obtain additional information regarding the subject or the capsule. For example, the medical practitioner may provide information regarding symptoms experienced by the subject, for example via user input module 102. As another example, the processor 104 may obtain additional information regarding the subject or the desired treatment from a remote location, such as a remotely located medical facility or a suitable database, for example via transceiver 110.

At step 204, a vibration treatment protocol is generated for the subject at the control unit 100, based on the input received from the user via user input module 102 and on additional input obtained by processor 104, for example from a medical practitioner or from a database. The vibration treatment protocol is programmable into a programmable vibrating ingestible capsule, such as capsule 130.

In some embodiments, the generated protocol specifies times at which the capsule should vibrate, and parameters for such vibration.

In some embodiments, the input obtained from a medical practitioner or medical facility indicates that the capsule should provide a sham capsule treatment. In some such embodiments, the treatment protocol specifies that the capsule should not vibrate following ingestion thereof.

Turning to step 206, it is seen that a programmable vibrating ingestible capsule is programmed to implement the vibration treatment protocol generated at step 204. In some embodiments, programming includes wirelessly transmitting the vibration treatment protocol from the programming module 106 of the control unit 100 to a transceiver or receiver 138 of the programmable vibrating ingestible capsule via transceiver 110 of the control unit, substantially as described hereinabove.

It will be appreciated that, in some embodiments, one or more vibration treatment protocols may be pre-programmed into a vibrating ingestible capsule, such as capsule 130. In some such embodiments, step 204 may be obviated. In embodiments in which a single vibration treatment protocol is pre-programmed into the capsule, step 206 may also be obviated. In embodiments in which the capsule is pre-programmed with multiple vibration treatment protocols, programming the capsule at step 206 includes indicating to the capsule which of the pre-programmed vibration treatment protocols should be used.

At step 208, the programmed programmable vibrating ingestible capsule is verified and activated to carry out the vibration treatment protocol. In some embodiments, verifying and activating the capsule includes transmitting a wireless activation signal from the control unit 100 to the capsule 130, for example via transceivers 110 and 138, and observing a response of the capsule 130 which is indicative of the capsule receiving the signal and being properly programmed and ready for operation. In some embodiments, the response of the capsule includes the capsule vibrating for a predetermined duration or in accordance with a specific pattern which is indicative of the capsule receiving the activation signal and being ready for operation.

It is a particular feature of the teachings herein that if the capsule is verified and activated, as described hereinabove, in the presence of the subject, the subject can see, and if he is holding the capsule in his hand can even feel, that the capsule actually works, or vibrates.

At step 210 the programmed, verified, and activated capsule is provided to the subject for ingestion, after the user has experienced at least one psychosomatic neutralizing activity as described with respect to steps 200, 202, and 208. It will be appreciated that step 210 is included in embodiments in which steps 200-208 occur in a medical facility, factory, or other such location. However, in some embodiments, the capsule may be provided to the subject for use in the comfort of their own home, prior to steps 200-208, or in between two of these steps. In such embodiments, step 210 may be obviated. Subsequently, at step 212, operation of the vibration treatment protocol by components of the capsule begins following ingestion thereof by the subject. As discussed hereinabove, in some embodiments, the vibration treatment protocol is a placebo or sham treatment protocol, which does not include any vibration of the capsule following ingestion of the capsule by the subject.

As discussed hereinabove, the inventors have discovered that a treatment including use of a non-dissolvable sham capsule, independently or in combination with a vibrating capsule as described herein, results in a positive response rate when treating gastrointestinal disorders such as acute and chronic constipation and gastroparesis.

As such, according to an embodiment of the present invention, the method described hereinabove with respect to FIG. 2 may be modified to relate to a sham treatment.

According to such a modified method, a sham treatment for a subject suffering from a gastrointestinal disorder includes providing a non-dissolvable ingestible capsule to the subject, for example as described hereinabove with respect to step 210 of FIG. 2. In some embodiments, the non-dissolvable ingestible capsule may be similar to capsule 130 described hereinabove, which is configured so that it does not vibrate following ingestion thereof by the subject. However, in other embodiments, the non-dissolvable ingestible capsule may be any other non-dissolvable capsule, such as a non-vibrating capsule, or a capsule having no electronic or moving mechanism, such as a capsule including only a non-dissolvable exterior shell having an empty hollow therein.

The subject then ingests the non-dissolvable ingestible capsule, such that passage of the non-dissolvable ingestible capsule through the gastrointestinal tract of the subject treats the gastrointestinal disorder.

In some embodiments, a sham treatment using a non-dissolvable ingestible capsule may be suitable for treating any of a variety of gastrointestinal disorders, including acute constipation, chronic constipation, and gastroparesis.

In some embodiments, the sham treatment disclosed herein, and/or the placebo treatment, include administering to the subject a plurality of treatment sessions, where in each treatment session the subject is provided with a suitable capsule and ingests the capsule.

In some embodiments, administering a plurality of treatment sessions includes administering at least one treatment session per week, over a treatment period of at least two weeks, at least at least three weeks, at least four weeks, at least five weeks, at least six weeks, or at least eight weeks.

In some embodiments, administering at least one treatment session per week includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

In some embodiments, the non-dissolvable capsule may be a spherical capsule. In other embodiments, the non-dissolvable capsule may be an elongated capsule arranged along a longitudinal axis and having a generally circular cross section in a direction perpendicular to the longitudinal axis.

In some embodiments, the diameter of the spherical capsule, or of the circular cross section of the elongated capsule, is not smaller than 3 mm, not smaller than 4 mm, not smaller than 5 mm, not smaller than 6 mm, or not smaller than 7 mm In some embodiments, the diameter of the spherical capsule, or of the circular cross section of the elongated capsule, is not greater than 15 mm, not greater than 14 mm, not greater than 13 mm, not greater than 12 mm, or not greater than 11 mm.

Is some embodiments, the diameter of the spherical capsule, or of the circular cross section of the elongated capsule, is within the range of 3 mm-15 mm, 3 mm-14 mm, 3 mm-13 mm, 3 mm-12 mm, 3 mm-11 mm, 4 mm-15 mm, 4 mm-14 mm, 4 mm-13 mm, 4 mm-12 mm, 4 mm-11 mm, 5 mm-15 mm, 5 mm-14 mm, 5 mm-13 mm, 5 mm-12 mm, 5 mm-11 mm, 6 mm-15 mm, 6 mm-14 mm, 6 mm-13 mm, 6 mm-12 mm, 6 mm-11 mm, 7 mm-15 mm, 7 mm-14 mm, 7 mm-13 mm, 7 mm-12 mm, or 7 mm-11 mm.

In some embodiments, the length of the non-dissolvable capsule, along a longitudinal axis thereof, is in the range of 3 mm-30 mm, 3 mm-29 mm, 3 mm-28 mm, 3 mm-27 mm, 3 mm-26 mm, 3 mm-25 mm, 3 mm-24 mm, 3 mm-23 mm, 3 mm-22 mm, 3 mm-21 mm, 3 mm-20 mm, 4 mm-20 mm, 5 mm-20 mm, 6 mm-20 mm, or 7 mm-20 mm.

In some embodiments, the sham treatment may be combined with an active treatment to improve the subject's response rate. For example, the treatment may include two or more treatment sessions per week, where at least one of the treatment sessions is a session of sham treatment, and at least one of the treatment sessions is a session of active treatment. A combined treatment may include any suitable number of sham treatment sessions and any suitable number of active treatment sessions, provided that it includes at least one treatment session of each type.

As demonstrated in Example 1 hereinbelow, in some embodiments, the greater the number of treatment sessions administered to the user using a non-dissolvable capsule, the greater the treatment response rate observed, even if all the treatment sessions are sham treatment sessions. As such, ingestion of a non-dissolvable capsule functions as a treatment method having no side effects.

EXAMPLES

Reference is now made to the following example, which, together with the above description, illustrates the invention in a non-limiting fashion.

Example 1

A first clinical study was conducted, in which 77 subjects were treated with a sham treatment. The treatment protocol included sham treatment cycles including administering two sham capsules per week, repeated for a treatment duration of eight weeks.

A second clinical study was conducted, in which 92 subjects were treated with a sham treatment. The treatment protocol included sham treatment cycles including administering five sham capsules per week, repeated for a treatment duration of eight weeks.

In both clinical studies, during a two week run-in period preceding the initiation of treatment, the subjects reported each time they had a complete spontaneous bowel movement (CSBM), namely a bowel movement which occurred spontaneously and following which the subject felt fully relieved. The average number of complete spontaneous bowel movements experienced by the subject, per week, was set as the baseline for that subject.

During the eight week treatment duration, the subjects continued to report when they had a complete spontaneous bowel movement.

In both clinical studies, a subject was considered to have responded to the treatment, if in at least six of the eight weeks in the treatment duration, the number of complete spontaneous bowel movements experienced by the subjects had increased by at least one from the determined baseline.

The administered sham capsules were vibrating capsules programmed so that they do not vibrate in the gastrointestinal tract of the subjects. The administered capsules included a zinc-manganese dioxide alkaline battery, such as a AG3/LR41 button cell, commercially available from Daly-Station Battery Limited of Shenzhen Guandong, P.R China, as the power source, and a coin type eccentric vibration motor, such as a coin-type motor having the Product Part No. C0834L-066332017-2001 commercially available from Ineed HK Limited of Kowloon, Hong-Kong, as the inactive vibrating agitation mechanism.

The results of the two clinical studies are shown in Table 1.

TABLE 1

| Study | Number of sham participants | Number of sham responders | Percentage of sham responders |
| --- | --- | --- | --- |
| 2 capsules per week | 77 | 15 | 19.48% |
| 5 capsuled per week | 92 | 33 | 35.87% |

As seen in Table 1, in the first clinical study, fewer than 20% of the subjects responded to the treatment, according to the definition of response to the treatment provided hereinabove. In the second clinical study, more than 35% of the subjects responded to the treatment. The p-value of the results presented in Table 1, which represents the statistical significance of the increase in the number of responders between the first and second clinical studies, was computed to be 0.0186.

As such, it is evident from Table 1 that there is a correspondence between the number of sham capsules ingested per week and the response rate. Specifically, the results show, with statistical significance, that the greater the number of capsules ingested per week, the greater the response rate of the subjects. Thus, the sham treatment described above demonstrates a dose response similar to that of chemical treatments, in which the greater the treatment dose given to the subject, the greater the treatment efficacy.

Example 2

As mentioned above with respect to Example 2, a clinical study of sham treatment was conducted, in which 92 subjects were treated with a sham treatment. The treatment protocol included sham treatment cycles including administering five sham capsules per week, repeated for a treatment duration of eight weeks.

The administered sham capsules were vibrating capsules programmed so that they do not vibrate in the gastrointestinal tract of the subjects. The administered capsules included a zinc-manganese dioxide alkaline battery, such as a AG3/LR41 button cell, commercially available from Daly-Station Battery Limited of Shenzhen Guandong, P.R China, as the power source, and a coin type eccentric vibration motor, such as a coin-type motor having the Product Part No. C0834L-066332017-2001 commercially available from Ineed HK Limited of Kowloon, Hong-Kong, as the inactive vibrating agitation mechanism.

A second clinical study, testing placebo treatment, was conducted. In the clinical study of placebo treatment, 15 subjects were treated with a placebo treatment. The treatment protocol included sham treatment cycles including administering five sham capsules per week, repeated for a treatment duration of eight weeks.

The administered placebo capsules had a weight of approximately 2550 mg. The capsule shell was formed of Gelatin, Glycerin, and water, excipients included beeswax and soybean oil, and the active ingredient was 1759 mg of calcium carbonate. The disintegration time of the capsules was in the range of 22 to 60 minutes.

In both clinical studies, during a two week run-in period preceding the initiation of treatment, the subjects reported each time they had a complete spontaneous bowel movement, namely a bowel movement which occurred spontaneously and following which the subject felt fully relieved. The average number of complete spontaneous bowel movements experienced by the subject, per week, was set as the baseline for that subject.

During the eight week treatment duration, the subjects continued to report when they had a complete spontaneous bowel movement.

In both clinical studies, a subject was considered to have responded to the treatment, if in at least six of the eight weeks in the treatment duration, the number of complete spontaneous bowel movements experienced by the subjects had increased by at least one from the determined baseline. The data collected in the placebo treatment study also evaluated the percentage of subjects who experienced an increase of at least two complete spontaneous bowel movements from baseline, during at least six of the eight weeks of the treatment duration.

The results of the two clinical studies are shown in Table 2.

TABLE 2

| Study | Number of participants | Number of responders | Percentage of responders |
| --- | --- | --- | --- |
| Sham: one additional CSBM per week during 6 of 8 weeks | 92 | 33 | 35.87% |
| Placebo: one additional CSBM per week during 6 of 8 weeks | 15 | 3 | 20.0% |
| Placebo: two additional CSBM per week during 6 of 8 weeks | 15 | 0 | 0.0% |

As seen in Table 2, in the sham clinical study, more than 35% of the subjects responded to the treatment, according to the definition of response to the treatment provided hereinabove. In the placebo clinical study, 20% of the subjects responded to the treatment, when defined for one additional CSBM per week for 6 of 8 weeks, and none of the subjects responded to the treatment when response was defined as two additional CSBMs per week for 6 of 8 weeks.

As such, it is evident from Table 2 that sham treatment has a higher response rate than a placebo treatment, indicating that treatment with sham capsules alone, even without vibrating ingestible capsules, is advantageous and improves symptoms of chronic constipation.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for treating a human subject suffering from a gastrointestinal disorder using a non-dissolvable ingestible capsule, the method comprising:
   providing the non-dissolvable ingestible capsule to the subject;
   and
   subsequently, ingesting the non-dissolvable ingestible capsule by the subject,
   wherein passage of said non-dissolvable ingestible capsule through the gastrointestinal tract of the subject treats the gastrointestinal disorder,
   and wherein said non-dissolvable ingestible capsule comprises a vibrating ingestible capsule operative in accordance with a vibration protocol, which vibration protocol is devoid of vibrations within the gastrointestinal tract of the subject.

2. The method of claim 1, further comprising, prior to said ingesting, triggering demonstrative vibrations of the vibrating ingestible capsule in the presence of the subject, such that the subject observes or feels said demonstrative vibrations.

3. The method of claim 1, further comprising providing to said vibrating ingestible capsule, using a control unit functionally associated with said vibrating ingestible capsule, information or an instruction regarding said vibration protocol.

4. The method of claim 3, wherein said control unit generates said vibration protocol and provides said vibration protocol to said vibrating ingestible capsule as said information.

5. The method of claim 4, wherein said control unit receives, prior to generating said vibration protocol, input relating to at least one desired parameter of treatment with said vibrating ingestible capsule, and generates said vibration protocol based on said received input.

6. A method for treating a human subject suffering from a gastrointestinal disorder, the method comprising:
   administering to the subject at least one sham treatment session using a non-dissolvable ingestible capsule, including;
   providing the non-dissolvable ingestible capsule to the subject; and
   subsequently, ingesting the non-dissolvable ingestible capsule by the subject; and
   administering to the subject at least one active treatment session using a vibrating ingestible capsule, including:
   providing said vibrating ingestible capsule to the subject, the capsule including:
   a housing;
   a battery, disposed within said housing; and
   a vibrating agitation mechanism, powered by said battery, said vibrating agitation mechanism adapted such that, in a first vibrating mode of operation, said housing exerts vibrations on an environment surrounding said capsule;
   ingesting said vibrating ingestible capsule by the subject; and
   following ingestion of said vibrating ingestible capsule by the subject, controlling said vibrating agitation mechanism such that said vibrating ingestible capsule vibrates in said first vibrating mode of operation when said capsule is disposed within a targeted zone within a gastrointestinal tract of the subject.

* * * * *